United States Patent [19]

Langford

[11] 4,206,204

[45] Jun. 3, 1980

[54] IODOPHOR COMPOSITIONS CONTAINING TERTIARY AMINE OXIDES

[75] Inventor: Philip W. Langford, Bristol, England

[73] Assignee: Tenneco Chemicals, Inc., Saddle Brook, N.J.

[21] Appl. No.: 839,228

[22] Filed: Oct. 4, 1977

Related U.S. Application Data

[63] Continuation-in-part of Ser. No. 635,396, Nov. 26, 1975, abandoned.

[30] Foreign Application Priority Data

Nov. 29, 1974 [GB] United Kingdom ............... 51844/74
Aug. 28, 1975 [GB] United Kingdom ............... 35552/75

[51] Int. Cl.$^2$ .............................................. H61L 13/00
[52] U.S. Cl. .................................... 424/150; 424/325; 258/106
[58] Field of Search .......................................... 424/150

[56] References Cited

U.S. PATENT DOCUMENTS

| 3,028,299 | 4/1962 | Wimcov et al. | 424/150 |
| 3,240,711 | 3/1966 | Wittmer | 252/106 |
| 3,380,923 | 4/1968 | Beach | 424/150 |
| 3,534,102 | 10/1970 | Waldstein | 260/584 |

OTHER PUBLICATIONS

McCutcheon's Detergents & Emulsifiers, p. 65, 1971.
Chemical Abstracts 62:13034g (1965).
Kirk–Othmer–Encyclopedia of Chemical Technology, 2nd Ed., pp. 32–33 (1971).

*Primary Examiner*—Leonard Schenkman
*Attorney, Agent, or Firm*—James P. Scullin

[57] ABSTRACT

The microbicidal activity of iodophors is enhanced by the inclusion therein of certain alkyl and alkoxyalkyl tertiary amine oxides. The presence of the tertiary amine oxides also enhances the retention of the amount of available iodine during storage. The improved iodophors are useful as disinfectants for surfaces, tools, and utensils, and as surgical scrubs.

15 Claims, No Drawings

IODOPHOR COMPOSITIONS CONTAINING TERTIARY AMINE OXIDES

This is a continuation-in-part of my copending application Ser. No. 635,396 filed Nov. 26, 1975 now abandoned.

SUMMARY OF THE INVENTION

This invention relates to improved iodophors which have particular value in combatting micro-organisms and in sterlising and disinfecting surfaces, instruments, utensils and other objects which may have come in contact with such micro-organisms including pathogenic bacteria, fungi, viruses and yeasts, and in use as surgical scrubs. In particular, the invention provides improved iodophors which combine the desirable features of long term stability, a high level of bactericidal and fungicidal activity against a wide spectrum of pathogenic micro-organisms, and particularly high activity against acid fast bacteria.

The novel compositions of this invention comprise iodine solubilized with surfactants and certain tertiary amine oxides together with other ingredients.

The invention also relates to methods for the preparation of such useful iodophors and to their use for bactericidal and fungicidal purposes.

BACKGROUND OF THE INVENTION

The high germicidal activity of elemental iodine is well known, but its low solubility in water (1 part in 3,450 at 20° C.) militates against its use in aqueous antiseptics. It is used in aqueous alcohol solution as tincture of iodine, but such preparations are not suitable for sterilizing surfaces, instruments, utensils etc., and when used as disinfectants on open wounds, cuts and abrasions, cause irritation and discomfort due to the rapid evaporation of the alcohol and precipitation of the iodine. Moreover, such preparations cause undesirable staining of the skin or other surfaces with which they come in contact.

Cantor and Shelansky in 1951 discovered that certain surfactants had the property of complexing with elemental iodine to yield molecular aggregates or micelles which on dilution with water yielded the free iodine in a germicidally active form. Such complexes were termed 'iodophors' and they have become important commercial disinfectants and sterilizing agents.

An inspection of the voluminous patent literature relating to iodophor compositions makes it clear that many surfactants are capable of solubilizing iodine. Thus, quaternary ammonium compounds are disclosed for this purpose in British Pat. No. 625,676. (West Laboratories Inc.); long chain alkyl phenol-ethylene oxide condensates are the non-ionic surfactants employed in the compositions covered by British Pat. No. 950,954 (West Laboratories, Inc.), in U.S. Pat. No. 2,989,434, (G. A. Brost, F. Krupkin and F. Woodward) and in British Pat. No. 923,114 (W. C. Evans & Co.). Condensates of ethylene oxide and aliphatic ethers or glycols are the preferred non-ionic surfactants employed as iodine solubilizers in the compositions referred to in U.S. Pat. No. 3,326,806 (G. P. Dolby) and in Netherlands Patent Application No. 64.12604 (W. C. Evans & Co.). Anionic surfactants have also been employed as iodine solubilizers, for example, in the iodophor compositions featured in U.S. Pat. Nos. 3,650,966 (R. L. Bakka) and 3,240,711 (G. C. Wittwer).

Mixtures of surfactants have also been employed, e.g. the mixture of poly-(vinyl pyrrolidine) and ethoxylated nonyl alcohol in German Offen. No. 2,105,057 (A. Halpern.).

Other publications which disclose iodine/surfactant combinations include: British Pat. Nos. 703,091 (General Aniline & Film Corp.); 962,955 (Bendix Corp.); 1,004,282 (West Laboratories, Inc.); 1,066,437 (W. C. Evans & Co.); 1,167,743 (West Laboratories, Inc.); 1,293,407 (BASF Wyandotte Corp.); 1,311,952 (Marles-Kuhlemann-Wyandotte); and U.S. Pat. No. 3,380,923 (M. D. Beach).

Iodine/alkoxylated alkylamine oxide compounds are disclosed in U.S. Pat. No. 3,534,102 (D. A. Waldstein), and iodine/amine compositions are disclosed in British Pat. Nos. 1,186,177 (Diversey Development Ltd.) and 1,316,571 (Dipenidam Ltd.).

In general, non-ionic surfactants have been preferred since the germicidal action of iodophors formulated with them is less adversely affected by the hardness of the water used to dilute them for use.

Not all the elemental iodine complexed in iodophor compositions is made available on dilution and it is a very desirable feature of such compositions that the ratio of available iodine (as determined by titration with standard thiosulphate solution) to total iodine should be as close to unity as possible without creating instability and that this ratio should not be reduced significantly on storage. The compositions to which this patent relates are characterized by a high ratio of available to total iodine and excellent storage stability. Furthermore they can contain a greater percentage of both total and available iodine than the great majority of commercial iodophors.

The germicidal activity of elemental iodine, it is known, is enhanced at low pH, and iodophors are generally formulated with the addition of an acid. Because of its good anticorrosion properties and buffering action, phosphoric acid is particularly useful in this respect. In one embodiment of this invention, a mixture of sulphuric acid and phosphoric acid is used to control the pH at or near the optimum level.

Hitherto, it has been found that the germicidal action of diluted iodophors is due solely to the elemental iodine released and that the activity of iodophor disinfectants can be accurately predicted from the known activity of aqueous or aqueous/alcohol solutions of iodine of similar iodine concentration.

I have now found that the use of certain tertiary amine oxides as co-solubilisers confers a synergistic bacterial action on iodophor compositions to give formulations which are much more active against certain pathogens, particularly the acid fast bacteria, than any hitherto disclosed iodophor.

A further advantage of the compositions to which this patent relates is that the tertiary amine oxide functions as a stabilizer as well as a synergistic solubilizing agent in combination with surfactants, and such compositions show a high and stable ratio of active to total iodine.

DETAILED DESCRIPTION OF THE INVENTION

The tertiary amine oxides suitable for use in the compositions according to this invention are those having the general formula:

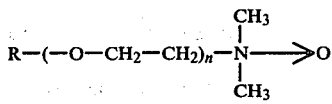

where R is an alkyl group having from about 10 to about 18 carbon atoms and mixtures thereof, and n is an integer from 0 to 4.

Examples of suitable tertiary amine oxides for carrying out this invention include N,N-dimethyl decylamine N-oxide; N,N-dimethyl undecylamine N-oxide; N,N,-dimethyl dodecylamine N-oxide; N,N-dimethyl tridecylamine N-oxide; N,N-dimethyl tetradecylamine N-oxide; N,N-dimethyl hexadecylamine N-oxide; N,N-dimethyl octadecylamine N-oxide; N,N-dimethyl 4-ethyldecylamine N-oxide; N,N-dimethyl 6,8-dimethyldecylamine N-oxide; N,N-dimethyl 6,7-dimethyloctylamine N-oxide; N,N-dimethyl decycloxyethylamine N-oxide; N,N-dimethyl decyloxyethoxyethylamine N-oxide; N,N-dimethyl decyloxyethoxyethoxyethylamine oxide; and N,N-dimethyl decyloxyethoxyethoxyethoxyethylamine N-oxide. Preferred examples are N,N-dimethyl cocoamine N-oxide (the N-oxide of a dimethyl tertiary amine derived from coconut oil fatty acids), and a mixture wherein n in the above general formula is 3 and R is a mixture of $C_{10}$, $C_{12}$, $C_{14}$, $C_{16}$, and $C_{18}$ alkyl groups, with $C_{12}$ alkyl groups predominating.

I prefer to use a single tertiary amine oxide in making the novel disinfectant compositions, or iodophors, of this invention, but mixtures of two or more can be employed if desired.

As co-solubilizer in conjunction with the claimed tertiary amine oxides, non-ionic surfactants are preferred. Particularly useful nonionic surfactants are the condensation products of ethylene oxide, or combination of ethylene oxide and propylene oxide, with long chain aliphatic alcohols. However, it is known that a variety of anionic, cationic and nonionic surfactants can act as iodine solubilizers and it is not intended that the scope of this invention should be limited to particular types of surfactants or mixtures. Thus, the co-solubilizer can be one or more nonionic, anionic, or cationic surfactant or any combatible mixture thereof. The essential feature is the inclusion, with the co-solubilizer, of a tertiary amine oxide. The tertiary amine oxide functions not only as a solubilizer of iodine, but also to enhance the stability as shown by maintaining the amount of available iodine, and to enhance the microbicidal activity of the composition.

A preferred class of nonionic surfactants comprises the condensation of fatty alcohol having from about 8 to about 20 carbon atoms, and especially from about 10 to about 15 carbon atoms, with from about 8 to about 12 moles of ethylene oxide or with a combination of ethylene oxide and propylene oxide. For applications in which a disinfectant having a high propensity to foam is not a disadvantage, or in which foaming is desirable, nonionic surfactants prepared with ethylene oxide are preferred.

For the preparation of high-foaming iodophors, a particularly preferred nonionic surfactant is one made by condensing n-decanol with 9 moles of ethylene oxide. Another preferred nonionic surfactant is that prepared by the condensation of one mole of nonylphenol with about 12 moles of ethylene oxide.

The iodophor compositions which are the subject of this invention function most effectively at low pH, and it is a preferred feature of these compositions that sufficient acid selected from the group consisting of hydrochloric acid, sulphuric acid, phosphoric acid, sulphamic acid, hydroxyacetic acid and citric acid or mixtures thereof, is incorporated so that a 1% aqueous solution has a pH of 6 or less, preferably between 1 and 4.

Particularly preferred is a mixture having a weight ratio of about 3 parts of sulphuric acid and about 2 parts of phosphoric acid. In place of the foregoing preferred acids, any water soluble acid can be used without departing from the scope of this invention.

It is particularly preferred that the compositions also include a minor amount of at least one water-soluble iodide selected from the group consisting of hydrogen iodide and inorganic iodides, such as potassium iodide, sodium iodide, or calcium iodide. Potassium iodide is preferred.

The iodine concentrate comprising the iodine dissolved in the surfactant-amine oxide mixture and containing the added acid, and if desired, the water soluble iodide, is dissolved for use in a liquid medium. Generally, this is water and the production and use of aqueous solutions of iodophors claimed for sterilising and disinfecting surfaces, instruments, utensils, and other objects is a particular feature of this invention. For certain purposes, a monohydric, dihydric, or polyhydric alcohol, or a mixture of these or aqueous solutions of these or their mixtures, may be preferred as the diluting medium. Examples of suitable liquid media, in addition to water, include isopropanol, ethylene glycol, and glycerol.

When preparing an iodophor using a surfactant, a tertiary amine oxide, an acid, and a liquid medium according to this invention, the relative proportions of each ingredient are not critical and can be varied over wide limits. It is preferred to use from about 0.5 to about 6 percent by weight of iodine, from about 0.9 to about 12 percent by weight of tertiary amine oxide, from about 8 to about 35 percent by weight of surfactant, from about 0.3 to about 45 percent of acid, and the balance of from about 2 percent to about 90.3 percent by weight of liquid medium. The amount of acid should be sufficient that the pH of a 1% by weight aqueous solution of the iodophor composition is 6 or less, and preferably between 1 and 4.

Amounts of these ingredients which fall outside of the foregoing preferred limits can be used if desired without departing from the scope of this invention. The only critical limitation is the use of enough of the combination of tertiary amine oxide and surfactant to dissolve the iodine and maintain it in solution, and enough tertiary amine oxide to obtain the benefits of improved retention of the amount of available iodine during storage, and improved microbicidal activity. It is preferred not to use an excess of tertiary amine oxide, due to its cost.

When a water soluble iodide is employed, it is preferred that the amount be from about 0.2 to about 5 percent by weight based on the total weight of the iodophor composition. Greater or lesser amounts can be used if desired, without departing from the scope of this invention.

In preparing the compositions of this invention, the order of addition of the various ingredients is not critical, but can be varied as desired.

For example, the iodine can be dissolved in the tertiary amine oxide and the surfactant added subsequently; or the iodine can be dissolved in the surfactant, followed by the addition of the tertiary amine oxide; or the iodine can be dissolved in a mixture of surfactant and tertiary amine oxide. The liquid medium can be added at any convenient stage, before or after the addition of iodine. Once a homogeneous solution has been obtained, sufficient acid is added to bring the pH of a 1% by weight aqueous solution to 6 or less, preferably between 1 and 4. When a water soluble iodide is used it can be added to the composition at any convenient stage, although it is preferred to add it last.

The compositions can be analyzed for total iodine and for available iodine by any suitable analytical procedure, such procedures being well known to those skilled in the art. For the determinations of available iodine, I prefer titration with standardized sodium thiosulphate.

For use in destroying undesirable micro-organisms and for sterilizing and disinfecting surfaces, instruments, utensils and other objects, the iodine containing compositions or iodophors of this invention are generally employed as dilute solutions, preferably in water although other solvents can be used if desired. To accomplish the desired result, the dilute solution is applied to the surface, or the object to be disinfected is dipped into such a dilute solution for a sufficient period of time, or the dilute solution is otherwise applied to a locus contaminated with micro-organisms. The iodophors can also be used as surgical scrubs, in the same manner as conventional surgical scrubs.

The following examples illustrate the invention, but are not to be considered limitative thereof.

EXAMPLE 1

3.4 parts by weight of iodine were added to 19.6 parts of EMPIGEN OY (Regd. Trademark). (EMPIGEN OY is a comercially-available product from Albright & Wilson Ltd. and comprises a 25% aqueous solution of an amine oxide of the formula:

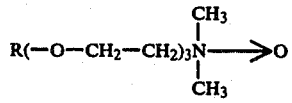

wherein R is a mixture of alkyl groups comprising from about 1.5 to about 4 weight percent $C_{10}$ alkyls, from about 51 to about 59 weight percent $C_{12}$ alkyls, from about 15 to about 25 weight percent $C_{14}$ alkyls, from about 5 to about 11 weight percent $C_{16}$ alkyls, and from about 6 to about 12 weight percent $C_{18}$ alkyls); the EMPIGEN OY had been heated to a temperature of not more than 40° C. To this was then added 19.4 parts by weight of a nonionic surface active agent of the formula $C_{10}H_{21}O-(OC_2H_4)_9-H$ with stirring. Finally, a solution of 13.3 parts by weight of sulphuric acid and 8.1 parts by weight of phosphoric acid in 36.2 parts by weight of water was added, again with stirring. The resultant iodophor had an available iodine content of 2.99 weight percent.

EXAMPLE 2

0.4 parts by weight of potassium iodide were stirred into 100 parts by weight of the composition prepared as described in Example 1. The available iodine content of the product of Example 2 was 3.20 weight percent.

EXAMPLE 3

This is a comparative example prepared according to the prior art, without tertiary amine oxide. In this example, 2.7 parts of iodine are dissolved in 13.5 parts of a nonylphenol/ethylene oxide concentrate. To this solution is added 2.0 parts of a solution of an alkyl quaternary ammonium chloride in isopropanol and water, 7.5 parts of phosphoric acid, 13.0 parts of sulfuric acid, and 61.3 parts of water. This yields an iodophor having an available iodine concentration of 2.16 weight percent.

In the foregoing examples, and in all other examples, the expression "parts" refers to parts by weight unless otherwise specified. In like fashion, "percent" or "%" refer to percent by weight unless otherwise specified.

The products of Examples 1, 2, and 3 along with a commercially-available iodophor which does not contain a tertiary amine oxide, and which has an available iodine content of 2.1%, were evaluated for biocidal activity using the following procedure.

TEST PROCEDURES

The compositions were tested as a general purpose disinfectant by the method of Section 3 (i) of the "Exemplary Note of the Approval of Disinfectants for the purpose of the Diseases of Animals Act 1950" published by the Ministry of Agriculture, Fisheries and Food, Department of Agriculture and Fisheries for Scotland. Details of the method are as follows:

The effective concentration of the disinfectant is that which, when added to a yeast organism misture, gives at least a $10^4$ reduction of titre. The Laboratory of the Government Chemist will determine the effective concentration by the following procedure.

The test is made using a 24-hour old culture of *Salmonella choleraesuis* (N.C.T.C. No. 10653 N.C.I.B. No. 10383) in an Oxoid No. 2 nutrient broth at 37°±1° C. and containing at least $10^8$ visible organisms per cm$^3$. Stock cultures of the test organism are maintained either in freeze-dried ampoules or on blood agar base slopes (Oxoid blood agar base) and prepared for use in accordance with B.S.S. 808 1938. The working culture is held at an incubation temperature of 37°±1° C. until just prior to its addition to the yeast suspension. A yeast suspension (5% dry weight) is prepared according to BSS. 808 1938 and held in cold storage until 4°±0.5° C. is reached. The disinfectant is diluted with sterile 342 ppm hard water (WHO formula) and reduced to a temperature of 4°±0.5° C.

To 96 cm$^3$ of the cold yeast suspension, 4 cm$^3$ of the working culture is added, mixed and dispersed in 2.5 cm$^3$ portions in an appropriate number of 15×150 mm Pyrex tubes with metal caps. To each tube is then added 2.5 cm$^3$ of the appropriate dilution of disinfectant also at 4°±0.5° C. and the mixture at once transferred to a fresh cooled tube. The tubes are held at a 4°±0.5° C. for 30 min. with shaking at 10 min. intervals. At the end of the 30 min. 0.1 cm$^3$ (5 drops from a standard 50 dropper) of the mixture is transferred to 10 cm$^3$ of nutrient broth (Oxoid No. 2) containing 5% horse serum. 1 cm$^3$ at this dilution (1 in 100) is added to each of 5×9 cm$^3$ nutrient broth (Oxoid No. 2) and incubated at 37°±1° C. for 48 hours. No growth in two or more of five broths=pass. Growth in more than three of five broths=fail.

The compositions were tested as a disinfectant for use against tuberculosis by the method of Section 3 (ii) of the same note.

Details of this method are as follows;

The effective concentration of the disinfectant is that which, when added to the yeast organism mixture, gives at least a $10^4$ reduction of titre. The laboratory of the Government Chemist will determine the effective concentration by the following procedure.

The test is carried out as laid down for general purpose disinfectants except that the test organism is a 7-day old culture of *Mycobacterium fortuitum* (N.C.T.C. No. 8573 N.C.I.B. No. 10384), the nutrient broth is Oxoid No. 2 plus 0.05% Tween 80, the contact time for the yeast-organism and disinfectant mixture is 60 min. at 4°±0.5° C. and the incubation period 7 days.

The compositions were tested as a disinfectant for use against Foot & Mouth Disease by the method of Section 3 of the same note.

Details of this test method are as follows:

The Animal Virus Research Institute carried out the following test:

The pH values of the disinfectant in W.H.O. hard water containing *Eagle's medium (10%) and ox serum (0%, 10% and 50%) were measured and the concentration of disinfectant estimated at which, in the presence of 50% ox serum, a 4 log. reduction in virus titre would be obtained (Sellers, 1968)**. A test was carried out by mixing foot-and-mouth disease virus with this concentration of disinfectant in W.H.O. hard water containing 10% ox serum. This mixture was held at 4° C. for 30 minutes and then further dilutions made for titrations of residual virus. The concentration under test gave a reduction of at least $10^4$ in virus titre.

(*Macpherson, I. A. and Stoker, M. G. P. (1962), Virology, 16,147.
**Sellers, R. F. (1968). Vet. Rec. 83,504).

The compositions were tested as a disinfectant for use against Fowl Pest by the method of Section 3 (iv) of the same note.

Details of the method are as follows:

The test carried out at the Central Veterinary Laboratory at Weybridge, was similar to that laid down for general purpose disinfectants except that the test organism was Newcastle disease virus, strain Herts 33. The test mixture was held at 4° C.±0.5° C. for 30 minutes and at the end of this time a dilution was made in 5% inactivated horse serum. Further dilutions were made for titration of the virus. The disinfectant under test gave a reduction of at least $10^4$ in virus titre.

The results of these tests are summarized in Table I, and show the surprising improvement in biocidal activity of the iodophors made according to the invention with tertiary amine oxide.

TABLE I

| | Effective Use Dilutions of Iodophors | | | |
|---|---|---|---|---|
| | Ex. 1 | Ex.2 | Ex. 3 | Commercial Iodophors |
| Foot and Mouth Disease | — | 1–400 | 1–240 | 1–220 |
| Swine Vesicular Disease | — | 1–300 | 1–160 | 1–180 |
| Fowl Pest | — | 1–180 | 1–90 | 1–80 |
| Tuberculosis | 1–90 | 1–100 | 1–30 | 1–11 |
| General Purpose Disinfectant | 1–180 | 1–180 | 1–85 | 1–90 |

In the following Examples 4 to 7 inclusive, the tertiary amine oxide was incorporated as a 25% solution of "Empigen OY", as in Example 1 above. Example 4 illustrates an iodophor containing an anionic surfactant, Example 5 one containing a cationic surfactant, namely the quaternary ammonium compound given, Example 6 one containing both a nonionic surfactant and a cationic surfactant and Example 7 one containing both an anionic surfactant and a nonionic surfactant.

EXAMPLE 4

| | |
|---|---|
| Iodine | 0.96 |
| Tertiary amine oxide (25% soln) | 7.8 |
| $C_{12}H_{25}O-(CH_2CH_2O)_3-SO_3Na$ (70% soln) | 12.0 |
| Orthophosphoric acid | 0.4 |
| Water | 78.84 |
| | 100.00 |
| Available iodine: 0.64% | |

EXAMPLE 5

| | |
|---|---|
| Iodine | 1.25 |
| Tertiary amine oxide (25% soln) | 11.3 |
| Cetyltrimethylammonium chloride (29% soln) | 41.5 |
| Orthophosphoric acid | 7.5 |
| Sulphuric acid | 11.7 |
| Water | 26.75 |
| | 100.00 |
| Available Iodine: 0.60% | |

EXAMPLE 6

| | |
|---|---|
| Iodine | 2.6 |
| Tertiary amine oxide (25% soln) | 10.7 |
| $C_{10}H_{21}O-(CH_2CH_2O)_9-H$ | 10.7 |
| Benzyl lauryl dimethyl ammonium chloride (50% soln) | 41.8 |
| Orthophosphoric acid | 7.5 |
| Sulphuric acid | 11.7 |
| Water | 15.0 |
| | 100.00 |
| Available iodine: 2.13% | |

EXAMPLE 7

| | |
|---|---|
| Iodine | 0.96 |
| Tertiary amine oxide (25% soln) | 3.9 |
| $C_{10}H_{21}O-(CH_2CH_2O)_9-H$ | 3.9 |
| Orthophosphoric acid | 0.36 |
| $C_{12}H_{25}O-(CH_2CH_2O)_3-SO_3Na$ (70% soln) | 12.0 |
| Water | 78.88 |
| | 100.00 |
| Available iodine 0.81% | |

Using the test procedures already described, the iodophors of Ex. 4 to 7 were tested for their effectiveness against *S. choleraesuis* and *M. fortuitum*. Pass results were obtained using 1 part of the iodophor to the amount of water indicated below.

| | Ex. 4 | Ex. 5 | Ex. 6 | Ex. 7 |
|---|---|---|---|---|
| S. chloraesuis | 1/25 | 1/35 | 1/80 | 1/35 |
| M. fortuitum | 1/20 | 1/20 | 1/100 | 1/20 |

EXAMPLE 8

| | |
|---|---|
| Iodine | 2.45 |
| Empigen OY (25% solution) | 66.0 |
| Orthophosphoric acid | 1.75 |
| 2-Propanol | 29.8 |
| | 100.00 |
| Available iodine 1.73% | |
| Pass dilution (*S. choleraesuis*) 1/30 | |

Pass dilution (*M. fortuitum* 1/80)

Example 8 is an example which does not contain a surfactant other than Empigen OY.

EXAMPLE 9

| Iodine | 5 |
|---|---|
| C₁₀H₂₁O—(OC₂H₄)₉—H | 22.5 |
| C₁₀₋₁₂H₂₁₋₂₅O—(OC₂H₄)₅—H | 5.5 |
| N,N-dimethylcoco amine oxide (40%) | 15.6 |
| (Aromox DMCD, Armour Hess Chemicals Ltd.) | |
| Orthophosphoric acid | 9.3 |
| Sulphuric acid | 15.0 |
| Water | 27.1 |
| | 100.00 |

Available iodine 3.81%
Pass dilution (*S. choleraesius*) 1/200
Pass dilution (*M. fortuitum*) 1/120

Example 9 is an iodophor made according to the invention with N,N-dimethyl alkylamine N-oxides (a mixture of homologs derived from coconut oil fatty acids) and a combination of two nonionic surfactants.

EXAMPLE 10

| Iodine | 0.95 |
|---|---|
| Empigen OY (25% solution) | 79. |
| Dodecyl benzene sulphonic acid | 8.4 |
| Orthophosphoric acid | 0.35 |
| 2-Propanol | 16.0 |
| Water | 66.4 |
| | 100.00 |

Available iodine 0.85%
Pass dilution (*S. choleraesius*) 1/50
Pass dilution (*M. fortuitom*) 1/35

Example 10 is an iodophor made according to the invention using an anionic surfactant.

EXAMPLE 11

| Iodine | 2.5 |
|---|---|
| C₁₀H₂₁O—(OC₂H₄)₉—H | 11.3 |
| C₁₀₋₁₂H₂₁₋₂₅O—(OC₂H₄)₅—H | 3.1 |
| Empigen OY (25% solution) | 14.4 |
| HI (50% solution) | 0.4 |
| Orthophosphoric acid | 2.4 |
| Glycerol | 40.0 |
| Water | 25.9 |
| | 100.00 |

Available iodine 2.3%
Pass dilution (*choleraesuis*) 1/110
Pass dilution (*M. fortuitum*) 1/75

Example 11 is an iodophor according to the invention made with a combination of two nonionic surfactants, an iodide, and with a combination of glycerol and water as the liquid medium.

EXAMPLE 12

| Iodine | 2.85 |
|---|---|
| C₉H₁₉C₆H₄O—(OC₂H₄)₁₂—H | 14.15 |
| Empigen OY (25% solution) | 13.25 |
| Orthophosphoric acid | 8.0 |
| Sulphuric acid | 13.0 |
| Water | 48.75 |
| | 100.00 |

Available iodine 2.15%
Pass dilution (*S. choleraesuis*) 1/90

Pass dilution (*M. fortuitum* 1/60)

Example 12 is an iodophor according to the invention made with a nonionic surfactant which is a condensation product of nonylphenol and ethylene oxide.

I claim:

1. In an iodophor composition comprising iodine dissolved in at least one surfactant selected from the group consisting of nonionic surfactants, anionic surfactants and quaternary ammonium cationic surfactants, an acid selected from the group consisting of hydrochloric acid, sulfuric acid, phosphoric acid, sulfamic acid, hydroxyacetic acid, citric acid and mixtures thereof, and a liquid medium selected from the group consisting of water, monohydric alcohols, polyhydric alcohols, and mixtures thereof, the improvement which comprises incorporating in said composition an amount sufficient to increase the biocidal activity of said composition of at least one tertiary amine oxide of the general formula

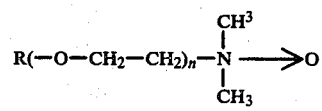

where R is an alkyl group having from about 10 to about 18 carbon atoms and mixtures thereof, and n is an integer from 1 to 4.

2. An iodophor composition according to claim 1 which also comprises a minor amount of at least one iodide selected from the group consisting of HI and water-soluble inorganic iodides.

3. An iodophor composition according to claim 1 wherein the tertiary amine oxide is a mixture in which R contains 10, 12, 14, 16 and 18 carbon atoms and in which n=3.

4. An iodophor composition according to claim 3 wherein R comprises from about 1.5 to about 4 weight percent $C_{10}$ alkyls, from about 51 to about 59 weight percent $C_{12}$ alkyls, from about 15 to about 25 weight percent $C_{14}$ alkyls, from about 5 to about 11 weight percent $C_{16}$ alkyls, and from about 6 to about 12 weight percent $C_{18}$ alkyls.

5. An iodophor composition according to claim 2 wherein the iodide is potassium iodide.

6. An iodophor composition according to claim 2 wherein the iodide is HI.

7. An iodophor composition according to claim 1 which comprises from about 0.5 to about 4 percent by weight of iodine, from about 8 to about 35 percent by weight of surfactant, from about 0.3 to about 45 percent by weight of acid, from about 2 to about 90.3 percent by weight of liquid medium, and from about 0.9 to about 12 percent by weight of tertiary amine oxide.

8. An iodophor composition according to claim 7 which also comprises from about 0.2 to about 5 percent by weight of an iodide selected from the group consisting of HI and water-soluble inorganic iodides.

9. An iodophor composition according to claim 1 wherein the surfactant is a nonionic surfactant prepared by the condensation of one mole of n-decanol with about 9 moles of ethylene oxide.

10. An iodophor composition according to claim 1 wherein the surfactant is a nonionic surfactant prepared by the condensation of one mole of nonylphenol with about 12 moles of ethylene oxide.

11. An iodophor composition according to claim 1 wherein the surfactant is sodium dodecyloxyethoxyethoxyethyl sulfate.

12. An iodophor composition according to claim 1 wherein the surfactant is cetyltrimethylammonium chloride.

13. An iodophor composition according to claim 1 wherein the surfactant is benzyl lauryl dimethyl ammonium chloride.

14. A process for the control of micro-organisms in a locus which comprises applying to the locus a disinfecting amount of the iodophor composition of claim 1.

15. A process for the control of micro-organisms in a locus which comprises applying to the locus a disinfecting amount of the iodophor composition of claim 2.

* * * * *

UNITED STATES PATENT AND TRADEMARK OFFICE
CERTIFICATE OF CORRECTION

PATENT NO. : 4,206,204
DATED : June 3, 1980
INVENTOR(S) : Philip W. Langford

It is certified that error appears in the above—identified patent and that said Letters Patent is hereby corrected as shown below:

Col. 9, line 29, delete "79." and insert -- 7.9 --

Col. 10, line 3, "(M. fortuitum" should appear

-- (M. fortuitum) --

Col. 10, line 53, change "4 percent" to -- 6 percent --

Signed and Sealed this

Ninth Day of September 1980

[SEAL]

Attest:

SIDNEY A. DIAMOND

Attesting Officer

Commissioner of Patents and Trademarks